United States Patent
Morris

(10) Patent No.: US 10,525,217 B2
(45) Date of Patent: Jan. 7, 2020

(54) INHALER

(71) Applicant: Kind Consumer Limited, London (GB)

(72) Inventor: Stephen Wynford Morris, Sussex (GB)

(73) Assignee: KIND CONSUMER LIMITED, London (GB)

(*) Notice: Subject to any disclaimer, the term of this patent is extended or adjusted under 35 U.S.C. 154(b) by 212 days.

(21) Appl. No.: 15/320,430

(22) PCT Filed: Jun. 25, 2015

(86) PCT No.: PCT/GB2015/051847
§ 371 (c)(1),
(2) Date: Dec. 20, 2016

(87) PCT Pub. No.: WO2016/005728
PCT Pub. Date: Jan. 14, 2016

(65) Prior Publication Data
US 2017/0143918 A1 May 25, 2017

(30) Foreign Application Priority Data

Jul. 8, 2014 (GB) .................................. 1412130.5

(51) Int. Cl.
| | | |
|---|---|---|
| *A24F 47/00* | (2006.01) | |
| *A61M 15/00* | (2006.01) | |
| *A61M 15/06* | (2006.01) | |
| *A61M 16/20* | (2006.01) | |

(52) U.S. Cl.
CPC ....... *A61M 15/0091* (2013.01); *A24F 47/002* (2013.01); *A61M 15/009* (2013.01);
(Continued)

(58) Field of Classification Search
CPC .......... A61M 15/0013; A61M 15/0016; A61M 15/009; A61M 15/0091; A61M 15/0093; A61M 15/06; A61M 16/20; A24F 47/002
See application file for complete search history.

(56) References Cited

U.S. PATENT DOCUMENTS

| | | | | |
|---|---|---|---|---|
| 2005/0028812 A1* | 2/2005 | Djupesland | ....... | A61M 15/0091 128/200.21 |
| 2006/0150971 A1* | 7/2006 | Lee | ..................... | A61M 15/009 128/203.15 |

(Continued)

FOREIGN PATENT DOCUMENTS

| | | |
|---|---|---|
| JP | S55103129 A | 7/1980 |
| WO | 2011015825 A1 | 2/2011 |

(Continued)

OTHER PUBLICATIONS

International Search Report and Written Opinion dated Aug. 24, 2015 for Application No. PCT/GB2015/051847.

(Continued)

*Primary Examiner* — Valerie L Woodward
(74) *Attorney, Agent, or Firm* — Patterson + Sheridan, LLP

(57) ABSTRACT

An inhaler according to an embodiment has a breath operated valve with a valve element biased closed by a spring and a diaphragm arranged to deform when suction is applied to an outlet end generating low pressure above the diaphragm to lift the valve element against the biasing force of the spring allowing composition to flow out of the inhaler. The spring is a strip of resilient material forming a u-shape with a first arm extending from a position adjacent to the valve element along the diaphragm in a direction away from the outlet end so as to support the diaphragm to an apex where it extends away from the diaphragm into a second arm (Continued)

extending back towards the outlet end, the second arm engaging with the housing to generate a biasing force to urge the valve element closed.

9 Claims, 4 Drawing Sheets

(52) U.S. Cl.
CPC ........ *A61M 15/0013* (2014.02); *A61M 15/06* (2013.01); *A61M 16/20* (2013.01); *A61M 2205/8225* (2013.01)

(56) References Cited

U.S. PATENT DOCUMENTS

| | | | | |
|---|---|---|---|---|
| 2011/0315152 | A1* | 12/2011 | Hearn | A24F 47/002 131/273 |
| 2012/0138052 | A1* | 6/2012 | Hearn | A24F 47/002 128/202.21 |
| 2013/0056012 | A1* | 3/2013 | Hearn | A24F 47/002 131/273 |
| 2013/0061861 | A1* | 3/2013 | Hearn | A24F 47/006 131/329 |

FOREIGN PATENT DOCUMENTS

| | | |
|---|---|---|
| WO | 2014033438 A1 | 3/2014 |
| WO | 2014033439 A1 | 3/2014 |

OTHER PUBLICATIONS

United Kingdom Search Report dated Jan. 22, 2015 for Application No. GB1412130.5.

* cited by examiner

INHALER

The present invention relates to an inhaler.

In particular, the present invention relates to an inhaler comprising a housing with an outlet end; a reservoir of inhalable composition within the housing, the reservoir having an outlet; a breath operated valve with a valve element biased closed by a spring to selectively close the reservoir outlet, and a diaphragm arranged to deform when suction is applied to the outlet end generating low pressure above the diaphragm to lift the valve element against the biasing force of the spring to selectively open the reservoir outlet allowing composition to flow out of the inhaler at the outlet end.

Such an inhaler will subsequently be referred to as being "of the kind described".

A number of inhalers of the kind described are disclosed in our own earlier WO 2011/015825, WO 2011/015826, WO 2014/033438 and WO 2014/033439.

The present invention has been designed particularly for a simulated cigarette having a pressurised refillable reservoir with an inhalable composition containing nicotine. However, the invention is equally applicable to other types of inhaler for dispensing other medicaments. It may be applied to a non-pressurised reservoir such as an e-cigarette with a reservoir from which the product is released when a user sucks on the e-cigarette.

In the above disclosures, the diaphragm is supported by an elongate vane which extends axially along the middle of the diaphragm and provides it with the necessary rigidity. The vane has an integral tooth which projects through the diaphragm, the tooth having an edge which extends across the inhaler and which pinches a tube closed in order to close the reservoir. The spring is in the form of a coil spring which is positioned in a recess in the top of the vane above the valve element and engages with the housing to provide the biasing force.

This arrangement has a number of drawbacks. Firstly, the coil spring is a standalone component which is very small and awkward to handle in a manual assembly process. This is particularly so when a large quantity of these springs are supplied together and have to be untangled prior to assembly. The degree of movement between the fully open and fully closed position of the valve is relatively limited and a coil spring is not the most efficient spring arrangement to generate a high restoring force in this limited space. Also, in order to provide optimum sealing of the reservoir outlet, the straight edge of the tooth should maintain the correct alignment at all times. However, the coil spring is not able to generate any significant lateral force to restore the tooth to the central position in the event that it should be displaced from this position during assembly or use.

According to the present invention an inhaler of the kind described is characterised in that the spring is a strip of resilient material forming a U-shape with a first arm extending from a position adjacent to the valve element along the diaphragm in a direction away from the outlet end so as to support the diaphragm to an apex where it extends away from the diaphragm into a second arm extending back towards the outlet end, the second arm engaging with the housing to generate a biasing force between the arms to urge the valve element closed.

Replacing the coil-shape spring with this new spring provides a number of benefits. The separate vane and spring of the prior art are replaced by a single component as the first arm is able to support the diaphragm and therefore fulfil the function of the vane.

The elimination of the coil spring significantly reduces the assembly problems as the new spring is a more substantial component which can be more easily handled and will not become tangled up with other springs in the same way the coil springs do.

Further, the U-shape arrangement as defined is a much more efficient shape for generating a higher biasing force in a small inhaler as the resilient force is effectively generated by a small deflection of the apex of the spring which is amplified at the other end of the spring.

The new design of spring prevents binding. In a coil spring once all coils are compressed or 'coil bound' the spring becomes solid, and further displacement must be accommodated by deformation of any supporting structure and will result in bending of the valve element or vane. Any 'off set' (lateral bending) on the spring will attempt to bias the sealing of the valve element. A coil spring cannot generate its own lateral force whereas the new spring will resist lateral twist Further, because of the manner in which the arms extend back and forth along the inhaler via the apex, any lateral force tending to move one of the arms away from a central position will be strongly resisted at the apex which provides a strong restoring force against any such lateral displacement.

The valve element may be separate from the spring. However, preferably, the first arm has a downwardly depending projection forming the valve element. This projection may penetrate the diaphragm. However, preferably, the projection is surrounded by the diaphragm. This avoids the need for an opening in the diaphragm which must be sealed.

An example of an inhaler in accordance with the present invention will now be described with reference to the accompanying drawings, in which.

Figure 1:
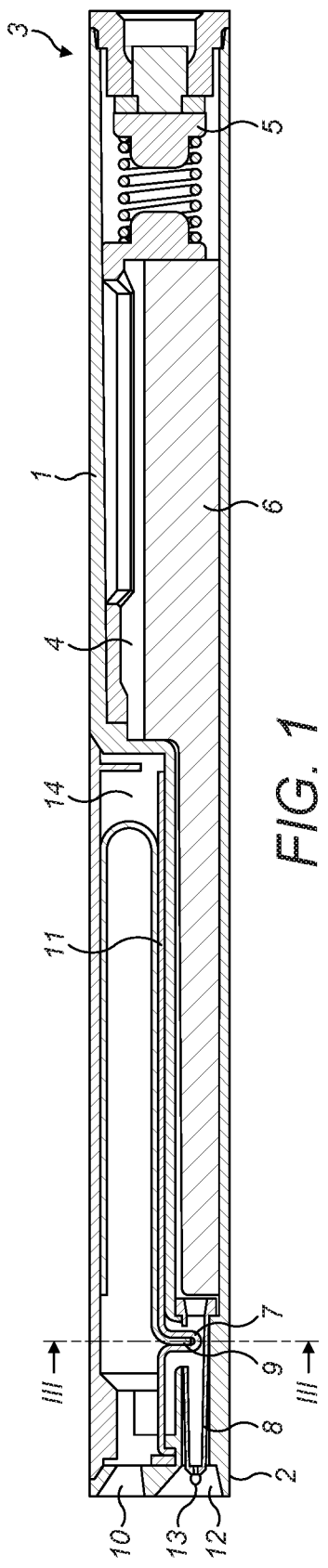
FIG. 1 is a cross-section of the inhaler.

The present invention relates to an improvement of the outlet valve for an inhaler such as that disclosed in WO 2011/015825, WO 2011/015826, WO 2014/033438 and WO 2014/033439.

The only difference from these disclosures relates to a new design of spring, and to a lesser extent, the diaphragm. The general inhaler design with therefore not be described in detail.

In general terms, the inhaler comprises a substantially cylindrical housing 1 which is intended to be the size and shape of a cigarette. The housing has an inhaling end 2 and a refill end 3. A pressurised reservoir 4 extends along the majority of the housing and is bounded at the refill end by a refill valve 5. As shown, the pressurised reservoir contains a wick 6 but may alternatively contain a tube as disclosed in PCT/GB2014/050939.

The opposite end of the reservoir is bounded by reservoir outlet 7 where a resilient tube 8 is pinched closed by a valve element 9 described in greater detail below.

At the outlet end 2 is an air outlet orifice 10 which leads into a chamber 14 above a diaphragm 11 such that suction on the outlet end 2 creates a low pressure in this chamber. Beneath the air outlet 10 is a composition outlet 12 through which the composition flows once the valve element 9 opens. A pair of secondary air outlets 13 (only one of which is shown in FIG. 1) draw air along the lower air outlet as described, for example, in WO 2014/033439.

Thus, suction on the outlet end causes a reduction in pressure in a chamber 14 above the diaphragm 11 causing the valve element 9 to lift thereby allowing composition to flow along the tube 8 and out of the composition outlet 12 whilst air from the air outlets 13 impinges on the composition.

To date, the operation of the inhaler is as described in the earlier disclosures.

The present invention is concerned with the manner in which the valve element 9 is biased and the interaction of this with the diaphragm. This will now be described with reference to FIGS. 2 to 5.

The diaphragm 11 forms the bottom wall of the chamber 14 and is formed of an elastomeric material which will deflect when the pressure in this chamber decreases. The valve element 9 is formed by a recess 20 in the diaphragm into which extends a projection 21 at the end of the U-shaped spring 22.

Figure 2:
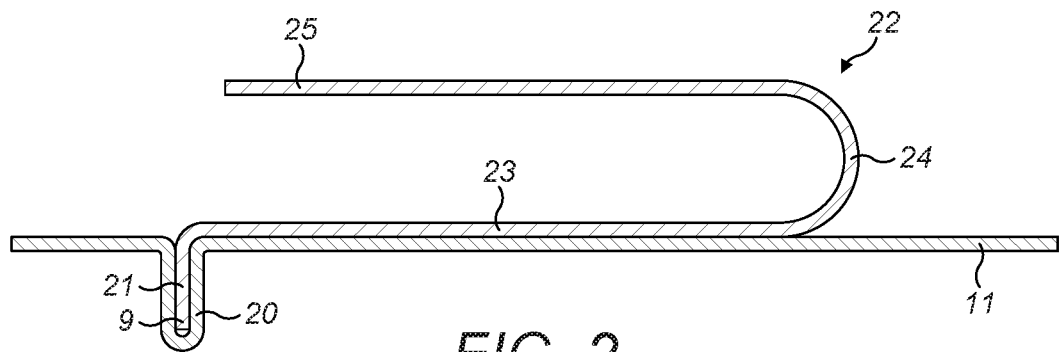
FIG. 2 is a cross-section through the spring and diaphragm in an axial plane.
Figure 3:
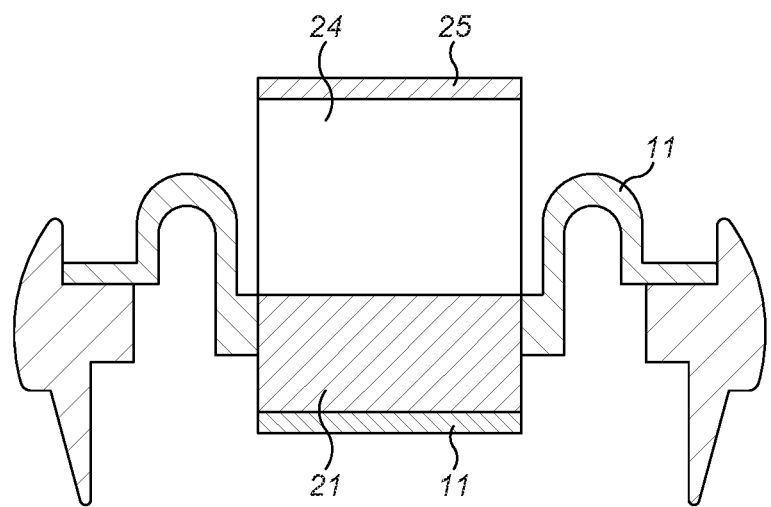
FIG. 3 is a cross-section through line III-III in FIG. 1.
Figure 5A:
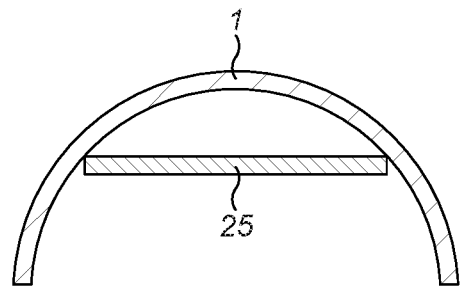
FIG. 5A is a cross-section through the upper housing and second arm in a radial plane.

As shown in FIG. 2, the spring 22 has a U-shaped configuration, a first arm 23 extending from the projection 21 along the diaphragm 11 away from the outlet end 2 such that it supports a central portion of the diaphragm thereby providing the necessary rigidity for the diaphragm 11 and replacing the vane of previous cases. The first arm 23 extends to an apex 24 where the spring extends away from the diaphragm 11 and towards the wall of the housing 1 curving round into a second arm 25 which extends back towards the valve element 9. This second arm 25 engages with the upper wall of the housing 1 as shown in FIG. 5A and is configured such that a compressive biasing force is generated between the two arms 23, 25 which maintains the valve closed.

When a user sucks on the outlet end, the low pressure in the chamber 14 causes a differential pressure across the diaphragm which overcomes the biasing force and lifts the valve element 9 to open the reservoir. This also causes the arms 23, 25 to approach one another thereby increasing the biasing force. When a user stops sucking on the outlet end, this increased biasing force ensures that the valve element 9 is pushed downwardly so that it returns to the closed position.

Figure 4A:
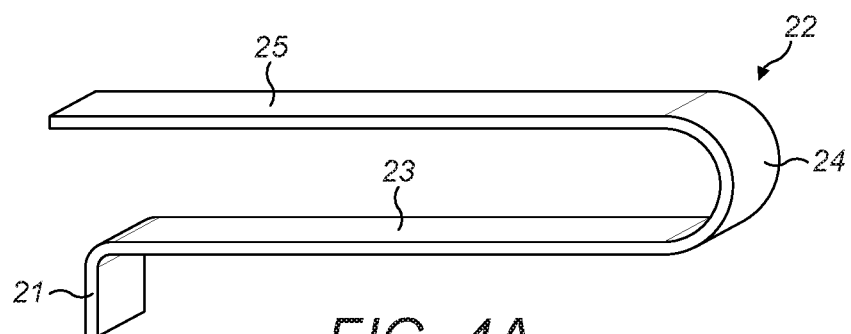
FIG. 4A is a perspective view of the spring.
Figure 4B:
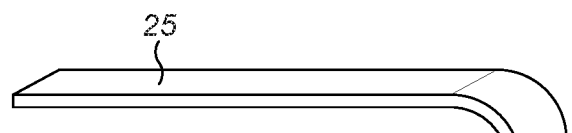
FIGS. 4B-4D show alternative configurations for a first arm.
Figure 4C:
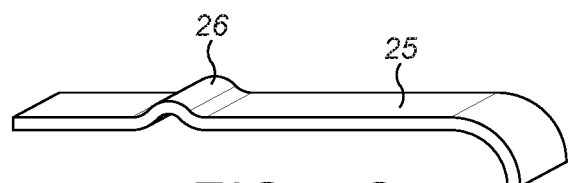
Figure 4D:
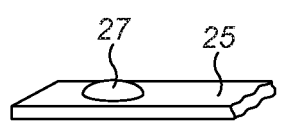

FIG. 4B shows the flat configuration of a second arm 25 as shown in FIG. 4A, while FIG. 4C shows the second arm with an outwardly extending kink 26 to enhance the engagement with the housing 1. FIG. 4D shows an alternative arrangement of the second arm 25 with an upwardly extending bump 27 also shown in FIG. 5C which provides enhanced engagement with the housing 1.

By providing some form of positive engagement point such as a kink 24 or bump 27 the second arm 25 positively engages with the housing 1 making its biasing force more consistent and reproducible. If the spring is left flat and square any sharp edge may dig into the platic of the housing and the spring may not be positioned correctly.

Figure 5B:
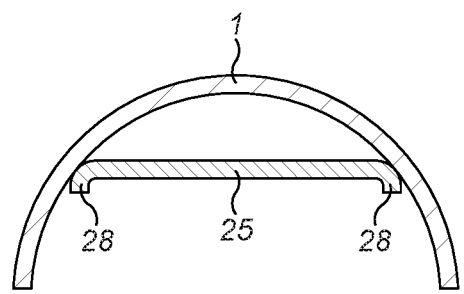
FIG. 5B is a view similar to FIG. 5A of a further second arm configuration.
Figure 5C:
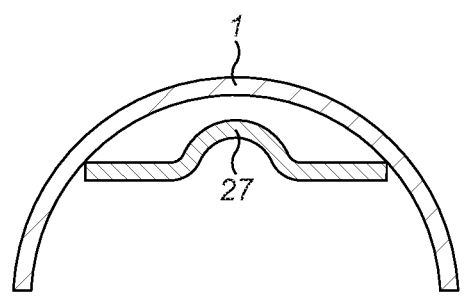
FIG. 5C is a view similar to FIGS. 5A and 5B of the second arm configuration of FIG. 4D.

FIG. 5B shows the second arm 25 having downwardly depending flanges 28 at either edge to enhance the rigidity of this arm.

Figure 4E:
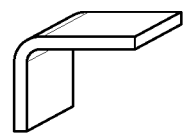
FIGS. 4E-4G show alternative configurations for the second arm.
Figure 4F:
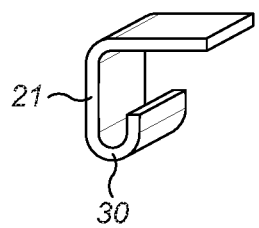
Figure 4G:
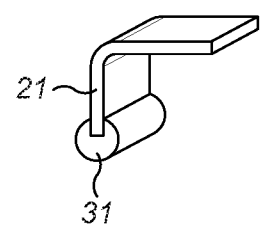

Different configurations of the first arm 23 are shown in FIGS. 4F and 4G (with FIG. 4E showing the unmodified configuration of FIG. 4A. FIG. 4F shows the end 30 of the spring bent up in a U-shaped configuration such that it provides a wider end which may be useful if the spring material is relatively thin and therefore liable to damage the diaphragm 11. A similar effect is achieved in FIG. 4G where a bead 31 is formed over the projection 21.

The more rounded tip may also provide a softer closing affect or be 'tuneable' in terms of seal ability.

The invention claimed is:

1. An inhaler comprising:
   a housing comprising an outlet end;
   a reservoir of inhalable composition within the housing, the reservoir having an outlet;
   a breath operated valve comprising a valve element biased closed by a spring to selectively close the reservoir outlet, and a diaphragm arranged to deform when suction is applied to the outlet end generating low pressure above the diaphragm to lift the valve element against the biasing force of the spring to selectively open the reservoir outlet allowing composition to flow out of the inhaler at the outlet end; and
   characterised in that the spring is a strip of resilient material forming a U-shape comprising a first arm extending from a position adjacent to the valve element along the diaphragm in a direction away from the outlet end so as to support the diaphragm to an apex where it extends away from the diaphragm into a second arm extending back towards the outlet end, the second arm engaging with the housing to generate a biasing force to urge the valve element closed.

2. An inhaler according to claim 1, wherein the first arm has a downwardly depending projection forming the valve element.

3. An inhaler according to claim 2, wherein the projection is surrounded by the diaphragm.

4. An inhaler according to claim 1, wherein the inhaler is a simulated cigarette with a substantially cylindrical housing.

5. An inhaler according to claim 1, wherein the reservoir is pressurised.

6. An inhaler according to claim 5, wherein the composition contains a propellant.

7. An inhaler according to claim 1, wherein the reservoir is refillable.

8. An inhaler according to claim 1, wherein the composition contains nicotine or a derivative thereof.

9. An inhaler according to claim 1, wherein the second arm is provided with a protrusion for engaging with the housing.

* * * * *